United States Patent [19]

Kodama et al.

[11] Patent Number: 5,459,046
[45] Date of Patent: Oct. 17, 1995

[54] CYTOCHROME C GENE DERIVED FROM HYDROGEN BACTERIUM

[75] Inventors: Tohru Kodama, Tokyo; Yasuo Igarashi, Saitama, both of Japan

[73] Assignee: Suntory Limited, Osaka, Japan

[21] Appl. No.: 943,140

[22] Filed: Sep. 10, 1992

Related U.S. Application Data

[63] Continuation of Ser. No. 486,409, Feb. 28, 1990, abandoned.

[30] Foreign Application Priority Data

Feb. 28, 1989 [JP] Japan ................................. 1-47427

[51] Int. Cl.⁶ ........................... C12P 21/06; C12P 21/04; C12N 1/20; C12N 1/14
[52] U.S. Cl. ...................... 435/69.1; 435/71.1; 435/71.2; 435/252.33; 435/254.2; 435/320.1; 536/23.2; 935/60; 935/68; 935/73
[58] Field of Search ..................................... 435/189, 192, 435/69.1, 252.3, 252.33, 849, 940, 911

[56] References Cited

FOREIGN PATENT DOCUMENTS 1-37291  2/1989  Japan.

OTHER PUBLICATIONS

Merchant et al., J. Biol. Chem. 262(19), 9062–9067 (1987).
Ishii et al., Agric. Biol. Chem., 51(6): 1695–1696 (1987).
Dumont et al (1987) Embo J. 6, 235–241.
Sanbangi, et al., J. Bacterial; 171, pp. 65–67, 1989.
Seiggs, et al., Proced. Natl. Acad. Sci.; 78, pp. 6613–6617, 1981.
McEwan, et al., Synthesis Of Rhodobacter Sphaeroides Cytochrome C2 In *Esherichia Coli*; Fems, Microbiology Letters 59, pp. 253–258, 1989.
Sanbong; et al. (1989) J. Bacteriol. 171, 65–69.
Suggs et al. (1981) Proced. Natl. Acad. Sci. 78, 6613–6617.

*Primary Examiner*—Jacqueline M. Stone
*Assistant Examiner*—Deborah Crouch
*Attorney, Agent, or Firm*—Cushman Darby & Cushman

[57] ABSTRACT

The nucleotide sequence of a DNA coding for highly thermophilic cytochrome C-552, a plasmid containing said sequence, a host cell transformed with said plasmid and a process for the production of C-552 comprising culturing said host.

3 Claims, 12 Drawing Sheets

Fig. 1

| | |
|---|---|
| AMINO ACID SEQUENCE | Gln-Lys-Gly-Cys-Met-Ala-Cys-His-Asp- |
| POSSIBLE CODON | CAR AAR GGN TGY ATG GCN TGY CAY GAY |
| PROBE 1 | 5' TGT ATG GCN TGT CAT GA 3' |
| PROBE 2 | 5' CAG AAG GGN TGT ATG GC 3' |

```
      1
5'  TCGGACCACGGGCAGGGGATACATCCCCTTCATACGGGCAGATG

50
    GTGAAAGAGGTGGACATAGAAGGTAAAAAAATCAAGGTATCTGA

100
    CATGCTTCAGAAAATCTACCCGTGAACTTCATCTTTGTTTCATAA

150
    AACTGTTTGTATTATAATATTGCAAACACTTTAAAAGGAGGTAG

200
    AGGCATGAAGAAGTTTCTGTTAGTAGCTGTAGTGGGGCTGGCAG
        M  K  K  F  L  L  V  A  V  V  G  L  A

250
    GCATAACCTTTGCCAATGAACAGCTTGCCAAGCAAAAGGCTGT
     G  I  T  F  A  N  E  Q  L  A  K  Q  K  G  C

300
    ATGGCTTGCCACGATCTGAAAGAAGCTAAGAAGGTGGGACCTTA
     M  A  C  H  D  L  K  K  A  K  K  V  G  P  Y

CGCAGATGTGTAGCTAAGAAGTATGCGGGAAGAAAGGATGCTGTTG
     A  D  V  A  K  K  Y  A  G  R  K  D  A  V
```

Fig. 2A-2

```
350
ATTATCTCTGGCTGGCAAGATAAAGAAGGGCCGGTTCTGTCTGTGG
 D  Y  L  A  G  K  I  K  K  G  G  S  G  V  W
        400
GGTTCTGTTCCCATGCCCTCCCTCAAAATGTAACCGATGCGGAAGC
 G  S  V  P  M  P  P  Q  N  V  T  D  A  E  A
        450
AAAACAGCTTGCCCAGTGGATACTCTCCATAAAGTAAGTTTTTG
 K  Q  L  A  Q  W  I  L  S  I  K  *  *  *
                          500
GGGCCGTTATGCCCTCCAGAGGATTACATCTCTGTTAATGTTTCCAA
                          550
AGCAATTAGGACATAGATCAAAAAACACCAGGAGTCCCAATCCT
                      600
CCCAGTCATCATGTTTACCTGAGTTATCACA
```

Fig. 2B

5'   TGGACCACCGGCAGGGGATACATCCCCTTCATAGGGCAGATG

GTGAAAGAGGTGGACACATAGAAGGTAAAAAAATCAAGGTATCTGA

CATGCTTCAGAAATCTACCCCGTGAACTTCATCTTTGTTTCATAA
                                   -35 SEQUENCE

AACTGTTTGTATTATAATATTGCAAACACTTTAAAAGGAGGTAG
         -10 SEQUENCE                  SD SEQUENCE

AGGC   3'

Fig. 2C

5'   ATGAAGAAGTTTCTGTTAGTAGCTGTAGTGGGGCTGGCAG
     M   K   K   F   L   L   V   A   V   V   G   L   A

GCATAACCTTTGCC   3'
 G   I   T   F   A

Fig. 2D

```
5'
     ATGGCTTGCCACGATCTGAAAGCTAAGAAGGTGGACCCTGCTTA
      M  A  C  H  D  L  K  A  K  K  V  G  P  A  Y

CGCCAGATGTAGCTAAAGAAGTATGCGGGAAGAAAGGATGCTGTTG
      A  D  V  A  K  E  V  C  G  K  K  D  A  V

ATTATCTGGCTGGCCAAGATAAAAAGATCAAAAAGGGGTTCTGGTGTGG
      D  Y  L  A  G  K  I  K  K  G  G  S  G  V  W

GGTTCTGTTCCCATGCCCCTCAAAATGTAACCGATGCCGAAGC
      G  S  V  P  M  P  P  Q  N  V  T  D  A  E  A

AAAACAGCTTGCCCAGTGGATACTCTCCATAAAGTAAG
      K  Q  L  A  Q  W  I  L  S  I  K  ***
```

Fig. 2E

5' AAGTTTTTGGGGCCGTTATGCCCTCCAGAGGATTACATCTG

TTAATGTTTCCAAAGCAATTAGGACATAGATCAAAAACA

CCAGGAGTCCCAATCCTCCCAGTCATCATGTTTACCTGAG

TTATCACA

B, BamHI; E, EcoRI; H, HindIII; HI, HincII; SalI; Sc, ScaI;

P6AP; GLYCERALDEHYDE-3-PHOSPHATE DEHYDROGENASE PROMOTER

Ptac; tac PROMOTER 1. cytochrome c-552
2. JM109 (no plasmid)
3. pKHC11, IPTG(-) LEADER(+)
4. pKHC 11, IPTG(+) LEADER(+)
5. pKHC 12, IPTG(-) LEADER(-)
6. pKHC 12, IPTG(+) LEADER(-)

1. cytochrome c-552
2. ΔCYC1, XS-30-2B
3. XS-30-2B
4. pYHC 11 LEADER(+)
5. pYHC 12 LEADER(-)

Fig. 8A WILD TIPE C-552

Fig. 8B RECOMBINANT C-552

Fig. 8C HORSE HEART CYTOCHROME C

WAVELENGTH (nm)

$-[\theta] \times 10^{-3}$

CYTOCHROME C GENE DERIVED FROM HYDROGEN BACTERIUM

This is a continuation of application No. 07/486,409, filed on Feb. 28, 1990, which was abandoned upon the filing hereof of the present application.

BACKGROUND OF THE INVENTION

This invention relates to a gene coding for cytochrome C-552 protein (hereinafter referred to simply as C-552), which is derived from a highly thermophilic and obligately autotrophic hydrogen bacterium *Hydrogenobacter thermophilus*, and a process for the production of C-552 by use of said gene.

PRIOR ART

Cytochrome C rapidly exchanges electrons with oxidoreductases such as cytochrome oxidases and cytochrome reductases. These electron exchange reactions are based on an oxidation-reduction reaction of heme iron. Recently attempts have been made to apply and develop these electron transfer reactions of metal proteins such as cytochrome C (e.g., J. Romisch et al., Eur. J. Biochem., 164, 111, 1987). These studies are aimed at the development of new materials imitating biological materials or elements, namely, biochips. It is expected that such a biochip will exert novel functions which could not be achieved by conventional semi-conductor elements. For example, biochips will be useful in the preparation of a catalytic electrode having biomolecular functions. At present, studies of electron transfer systems, wherein electrons are transferred by cytochrome C molecules aligned on the surface of a metal electrode in a solution, are in progress (H. A. O. Hill et al., J. Electroanal. Chem., 217, 141, 1987). It is believed that the positive charge on a lysine residue in the neighborhood of heme C plays an important role in this electron transfer (M. J. Eddowes, J. Am. Chem. Soc., 101, 7113, 1979).

The results of amino acid sequence analysis suggest that C-552 contains a number of lysine residues and that many of these lysine residues are located on the surface of the molecule, since the isoelectric point of C-552 is specifically high, compared with other proteins (Y. Sanbongi et al., J. Bacteriol., 171, 65, 1989). These characteristics of C-552 enable efficient electron transfer, which makes C-552 highly useful as an electrode element. Furthermore, C-552 is advantageous in that it can be accumulated at high density on the surface of an electrode since it has the lowest molecular weight among cytochromes C so far reported. Furthermore, C-552 is highly stable under heating and is not denatured at 120° C., unlike the other cytochromes C which are denatured at around 80° C. No known cytochromes C except C-552 has such desirable characteristics (Y. Sanbongi et al., J. Bacteriol., 171, 65, 1989).

Equine cytochrome C is effective in relieving myocardial infarction and cerebrovascular diseases such as cerebral hemorrhage and various symptoms caused by tissue oxygen deficiency, for example, carbon monooxide poisoning and dyspneal pulmonary diseases. It is expected that C-552, which has a lower molecular weight and a higher stability, may be more effective as such a drug.

It is considered that the expression level of C-552, which is a protein occurring in a periplasmic fraction of *Hydrogenobacter thermophilus* cells, is substantially high (Y. Sanbongi et al., J. Bacteriol., 171, 65, 1989). Thus it is assumed that the promoter, terminator and signal peptide which together control the expression of C-552 are highly efficient. Thus it will be useful if their structures are revealed.

C-552 is also useful in lowering the mutagen of, for example, food products. It has been reported that food products, in particular, coffee drinks sometimes contain mutagenicity. It has also been reported that such a mutagenicity can be reduced by adding a peroxidase to food products (Japanese Patent Laid-Open No. 62945/1985). However, known peroxidase are all unsatisfactory in terms of their heat resistance and no known peroxidase can retain its activity at a high temperature such as 80° C. or above for a period of time over 24 hours. Thus problems exist in practically applying such known peroxidases in the production of coffee drinks.

On the other hand, it is known that cytochrome C has a peroxidase activity. As described above, the hydrogen bacterium cytochrome C of the present invention is highly stable under heating and can retain its peroxidase activity at a high temperature for a prolonged period of time. It is therefore highly useful to employ the cytochrome C of the present invention in order to eliminate the mutagenicity of coffee drinks.

Hydrogen peroxide is known to be cytotoxic and carcinogenic. Cytochrome C of the present invention can be used to dissolve hydrogen peroxide under severer conditions and for a longer period of time as compared to a conventional peroxidase. Thus the cytotoxic and carcinogenic effects of hydrogen peroxide can be eliminated.

As described above, C-552 is a protein having excellent properties. However, *Hydrogenobacter thermophilus*, which is an obligately autotrophic bacteria utilizing hydrogen, needs to be cultured at approximately 70° C. under blowing of a gas mixture comprising hydrogen, oxygen and carbon dioxide into the medium. The culture temperature of approximately 70° C. raises the cost of production. In addition, this bacterium does not metabolize organic materials but requires hydrogen which is highly flammable. Therefore, a large scale cultivation of this bacterium can be dangerous. On the other hand, expression of C-552 in a host which can be cultured more easily will enable easier large scale production of the useful C-552 if the gene coding for C-552 could be obtained and treated by recombinant DNA techniques. As described above, the amino acid sequence of C-552 is already known. However, it is required to obtain C-552 gene and specify the nucleotide sequence thereof in order to solve the following problems. (1) A cytochrome C gene of a procaryote contains a sequence coding for the cytochrome C protein as well as a code sequence of a signal peptide which plays an important role during the biosynthesis of cytochrome C. It is, however, impossible to determine the sequence of this signal peptide based on the amino acid sequence of C-552. Thus it is imperative to determine the nucleotide sequence of the gene. (2) The results of an amino acid sequence analysis of a protein often include errors. Thus the exact amino acid structure cannot be determined until the nucleotide sequence of C-552 gene is specified. (3) Although the nucleotide sequence of a gene can, to some extent, be estimated based on the amino acid sequence, it is impossible to specify the exact sequence of the gene due to the degeneration of codons. Thus a synthetic DNA sequence is, in many cases, consequently not effectively expressed.

SUMMARY OF THE INVENTION

The present invention provides a C-552 gene, plasmids containing said gene, recombinant host cells transformed by said plasmid and a process for the production of C-552 by using said host cells.

C-552 is synthesized in vivo together with a signal peptide. According to the present invention, it is possible to produce said protein in a host such as yeast suitable for large scale culture, by taking advantage of said signal peptide. It is believed that C-552 is expressed in the cell at a significantly high level and hence it will be valuable to determine the structures of the promoter and terminator regions of C-552 which are responsible for the expression at such a high level. The signal peptide and promoter are particularly characteristic in that they can normally function even at a high temperature. Thus they will be useful in, for example, expression of a protein in an organism which grows at a high temperature.

The amino acid sequences of cytochromes C of procaryotes are less homologous with those of cytochromes C of eucaryotes and highly diverse (Dickerson, Scientific American, 242, 137, 1980). It is believed that the conditions under which C-552, namely, a typical cytochrome C of procaryotes is expressed would also allow the expression of other procaryotic cytochromes C. An example of such cytochromes C is cytochrome C3 of a sulfate reducing bacterium.

In order to achieve these objections as described above, the inventors attempted the cloning and structural analysis of C-552 gene and expression of said gene in yeast.

BRIEF DESCRIPTION OF THE DRAWINGS

FIG. 1 shows the sequences of synthetic probes for screening C-552 gene as well as the corresponding amino acid sequence and the possible codons.

FIG. 2A-1 and FIG. 2A-2 together show the nucleotide sequence of the C-552 gene including the promoter sequence, the signal sequence and the terminator sequence.

FIG. 2B shows the nucleotide sequence of the promoter region of the C-552 gene wherein the -35, -10 and SD sequences are underlined.

FIG. 2C shows the signal sequence of C-552 and the nucleotide sequence coding therefor.

FIG. 2D shows the translation region of C-552 and the nucleotide sequence coding therefor.

FIG. 2E shows the nucleotide sequence of the terminator of C-552 wherein a palindrome is underlined.

FIGS. 8A, 8B and 8C show the CD spectra of wild type cytochrome C-552, recombinant cytochrome C-552 and equine heart cytochrome C, respectively.

DETAILED DESCRIPTION OF THE INVENTION

Figure 3:
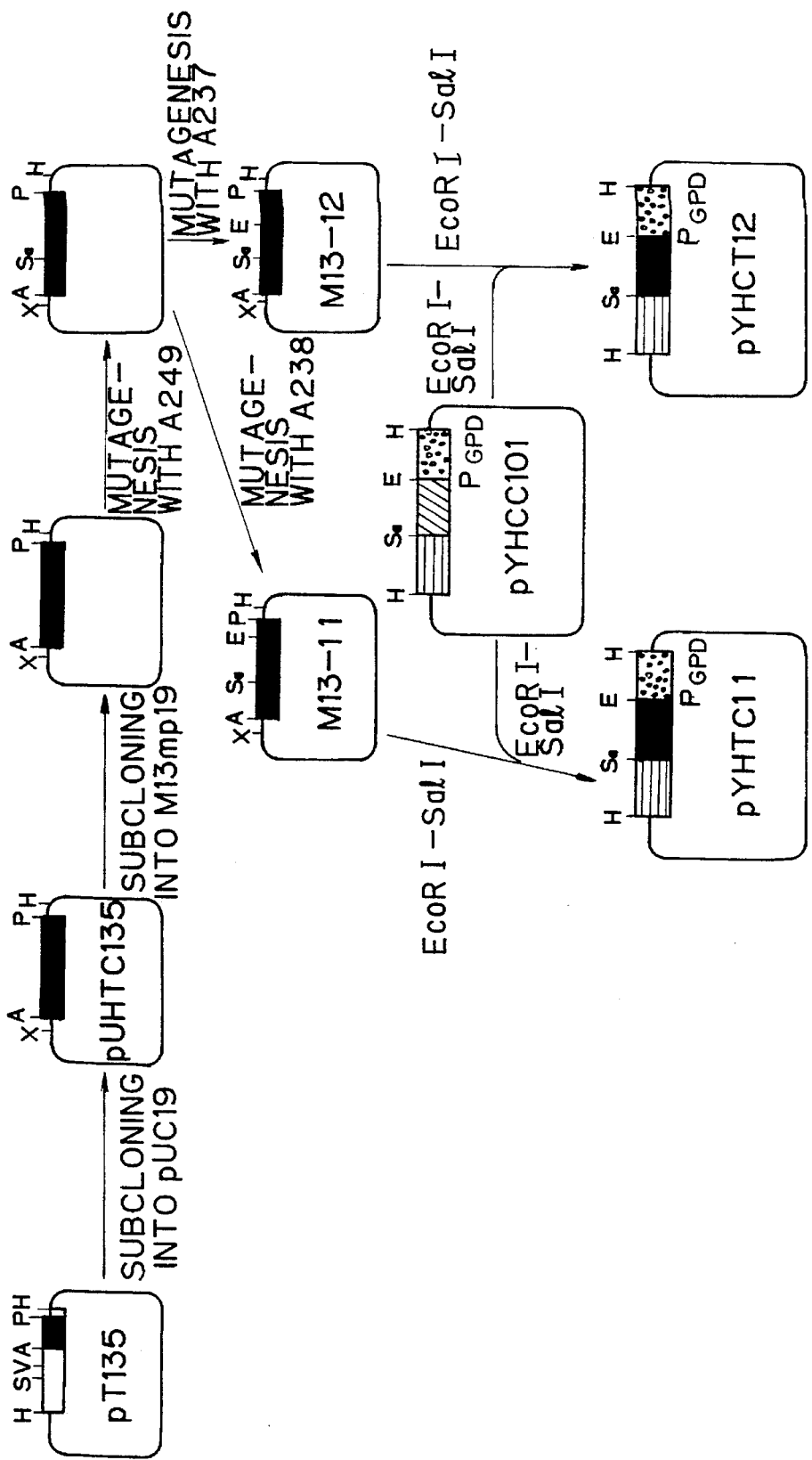
FIG. 3 briefly illustrates the preparation of plasmids employed in the expression of C-552 in yeast.

The inventors have isolated C-552 gene by DNA recombinant techniques and determined the nucleotide sequences of the structural gene, the signal sequence and the promoter and terminator.

Accordingly, the present invention provides a DNA sequence coding for *Hydrogenobacter thermophilus* C-552, the signal sequence thereof, the sequences of the promoter and terminator thereof, plasmids containing the same and host cells transformed by said plasmid.

The detail of the sequences are described in the above figures and claims hereinafter. When the term "a sequence is substantially represented by the formula" is used in the claims, we intend to mean that the sequence in question may differ from the specified sequence by one or more addition, deletion and/or substitutions of amino acids or nucleotides which may sometimes take place in nature but have no significant effect on the phenotype of the expression product.

The gene coding for C-552 protein can be obtained by, for example, the following method. Namely, two oligonucleotides were synthesized based on the nucleotide sequence of the gene deduced from the previously reported amino acid sequence of the protein. The oligonucleotides thus obtained were used as probes in the subsequent cloning of C-552 gene. Chromosomal DNA obtained from *Hydrogenobacter thermophilus* cells was digested with appropriate restriction enzymes, subjected to Southern blotting and then hybridized with the use of said synthetic oligonucleotides. As a result of the hybridization, the probes showed strong hybridization with a DNA fragment of 2.5 kb obtained by digesting the chromosomal DNA with restriction enzyme HindIII. This fragment was collected and subcloned into the HindIII site of pBR327 in order to transform *Escherichia coli*. A plasmid containing said fragment was obtained from the transformants. This plasmid was hybridized with the above-mentioned probes in the same manner as the one described above. A transformant containing a DNA capable of hybridizing with the probes was obtained.

This transformant had a plasmid which contained the DNA of 2.5 kb which could be excised with HindIII. Treatment of this plasmid by restriction enzymes and subsequent Southern blotting of the digested product were repeated. As a result, the two synthetic probes hybridized with a DNA fragment of 1.1 kb separated by AccI and PstI. The fragment was subcloned between the PstI and AccI sites of the cloning plasmid pUC19 commercially available from Takara Shuzo, Japan. The resulting plasmid was used as a template and the nucleotide sequences determined by using the synthetic nucleotides as primers. Thus the nucleotide sequences of the coding region, signal sequence and promoter and terminator regions of C-552 were determined (FIGS. 2A to 2E).

Next, expression of C-552 in yeast was studied. A SalI site was prepared immediately after the termination codon (TAA at 472 to 474 in FIG. 2A) of C-552 gene by site-specific mutation in order to introduce it into a vector for expression. Further, an EcoRI site was prepared immediately before the initiation codon (ATG at 178 to 180 in FIG. 2A) or alternatively an EcoRI site and an initiation codon ATG were prepared in the same manner immediately after the signal sequence (from A at 178 to C at 231 in FIG. 2A). One of these two DNA mutants thus prepared had a coding region of C-552 between the two restriction sites prepared as described above, while the other had said region together with a signal sequence. Then the DNA fragments isolated from these two DNAs by EcoRI and SalI digestion were respectively linked to a yeast expression vector. When the plasmids thus obtained were introduced into a yeast strain XS-30-2BΔCYC1, which is deficient in iso-1 cytochrome C gene CYC1 and thus cannot grow on lactic acid as a carbon source, the yeast transformed with each of these DNA mutants could grow on lactic acid as a carbon source. These results indicate that C-552 functioned instead of the iso-1 cytochrome C in the electron transfer system of the yeast. In other words, C-552 carrying heme C was produced in the yeast. It was not expected that yeast would express C-552 since it is a procaryote protein, is different in molecular weight and is low in terms of the homology of the amino acid sequences. Thus it is considered that yeast can express not only C-552 but also every cytochrome C of procaryotes as well as eucaryotes, for example, cytochrome C3 and cytochrome C2.

On the other hand, the DNA coding for C-552 could be linked to an *E. coli* expression vector and used to transform a strain of *E. coli*. One clone, which had the C-552 DNA but lacked the signal sequence, among the transformants was found to have expressed C-552. The resulting recombinant C-552 was comparable to the wild type C-552 of *Hydrogenobacter thermophilus* in terms of their excellent properties.

Therefore, use of the nucleotide sequence determined by the inventors will enable production of recombinant C-552 or production of proteins under high temperature conditions with the use of said promoter. Furthermore, culture of the recombined yeast will make it possible to produce a quantitative amount of C-552 of excellent properties. Now the present invention will be described in detail by reference to Examples. Unless otherwise specified, each experiment was conducted in accordance with the procedures described in "Molecular Cloning" (Maniatis et al., Cold Spring Harbor, 1982).

EXAMPLE 1

Cloning of C-552 Gene of *Hydrogenobacter thermophilus*

(1) Synthesis of Nucleotide Probes

Oligonucleotides were synthesized based on the 7th to 15th amino acid sequence (Gln-Lys-Gly-Cys-Met-Ala-Cys-His-Asp-) in the amino acid sequence of C-552 which had been already determined. Thus two groups of 17-mer oligonucleotides as shown in FIG. 1, i.e., probe 1 (5'TGTATG-GCNTGTCATGA3') and probe 2 (5'CAGAAGGGNTG-TATGGC3') were synthesized on a DNA synthesizer System-1 (Beckman). N means a mixture of G, A, T and C. The nucleotides thus obtained were purified in accordance with the method recommended by Beckman.

(2) Preparation of Chromosomal DNA of *Hydrogenobacter thermophilus*

The chromosomal DNA of *Hydrogenobacter thermophilus* was prepared in the following manner. 2 g of cells from a culture, were suspended in 20 ml of an STE buffer solution (20% saccharose, 10 mM Tris-HCl pH 8.0, 1 mM EDTA) and 80 mg of lysozyme was added thereto. The mixture was maintained at 37° C. for 10 minutes. Proteinase K was then added thereto so as to give a final concentration of 50 μg/ml and the mixture was maintained at 37° C. for 30 minutes. Next, 10% SDS was added thereto at a final concentration of 0.54 and further proteinase K at a concentration of 100 μg/ml. The mixture was maintained at 37° C. for 30 minutes. An additional portion of 104 SDS was added thereto so as to give a final concentration of 24 and the mixture was maintained at 50° C. for 60 minutes.

To the mixture so obtained, an equivalent amount of phenol/chloroform (Maniatis, Molecular Cloning) was added and the mixture was slowly stirred and centrifuged, followed by collecting the supernatant. This procedure was repeated three times. Then two volumes of ethanol were added, the mixture was centrifuged and the precipitated DNA was collected.

The DNA was suspended in 10 ml of a TE buffer solution (10 mM Tris-HCl pH 8.0, 1 mM EDTA) and RNase was added to give a final concentration of 20 μg/ml. The mixture was maintained at 37° C. for 30 minutes and dialyzed against the TE buffer solution. The chromosomal DNA solution thus obtained was used in the following tests.

(3) Southern Hybridization

Southern hybridization was conducted in the conventional manner. The chromosomal DNA fragment obtained as above was digested with restriction enzyme HindIII and subjected to agarose gel electrophoresis. Then the gel was blotted onto a nylon membrane Hybond-N (Amersham). The blot was then hybridized with the probe 1 or 2 labelled with {γ-$^{32}$P}ATP. The hybridized membrane was then exposed to a film in order to provide an autoradiogram.

The results of the autoradiography indicated that both of the probes were specifically hybridized with a fragment of 2.5 kb. Thus it was found that the C-552 gene was present in this DNA fragment.

(4) Subcloning

An agarose gel fraction containing the 2.5 kb HindIII fragment was excised and the DNA was recovered therefrom in a conventional manner.

On the other hand, pBR327, which is widely used as a vector for *Escherichia coli*, was digested with HindIII, treated with alkaline phosphotase in a conventional manner and then extracted with phenol/chloroform. This DNA fragment was linked to the above-mentioned 2.5 kb DNA fragment with a ligase in a conventional manner so as to transform *Escherichia coli* HB101 strain. The 159 transformants thus obtained were screened by colony hybridization with the use of the above-mentioned probes. Thus 11 positive clones were obtained.

Each of these 11 positive clones was cultured in a 2 ml volume and plasmid DNA was extracted in a conventional manner. Then this DNA was digested with HindIII and subjected to Southern hybridization. As a result, a plasmid capable of hybridizing with the two probes was obtained. This plasmid was named pT135. Digestion of pT135 with appropriate restriction enzymes and Southern hybridization were repeated. An AccI-PstI fragment of 1.1 kb eventually obtained was found to hybridize with both of the two probes.

This DNA fragment was ligated with pUC19 previously digested with AccI and PstI and used to transform *Escherichia coli* HB101. The resulting plasmid is referred to as pUHTC135.

The *Escherichia coli* transformed with said plasmid was named *Escherichia coli* SAM 1306. It was deposited with the Fermentation Research Institute, Agency of Industrial Science and Technology as FERM p-10546. This was converted to a deposition under the Budapest Treaty with the accession number FERM BP-2748 on Feb. 1, 1990.

(5) Specification of nucleotide sequence

The plasmid pUHTC135 was multiplied in a conventional manner. Then double stranded dideoxy sequence method was conducted by using this plasmid as a template and the probe 2 used in the screening and the reverse primer (Takara Shuzo, Japan) as primers to determine the nucleotide sequence of C-552. The double stranded dideoxy sequence method is described in detail in, for example, "Zoku Seikagaku Jikken Koza: Idenshi Kenkyu Ho I" (Takanami et al., Tokyo Kagaku Dojin). The nucleotide sequence thus determined (FIG. 2A) contained a region coding for the signal peptide of C-552, the promoter region and the terminator region.

The coding region including the signal region coded for 98 amino acids ranging from the initiation codon ATG (FIG. 2A, 178–180), where translation is initiated, to the termination codon TAA (FIG. 2A, 472–474) where the translation is terminated. The amino acid sequence of C-552, which was previously known, was initiated from the 19th asparagine (represented by N in FIG. 2A). The sequence following this asparagine completely agreed with the sequence of C-552 (FIG. 2D). The amino acid sequence ranging from the amino terminal to the 18th amino acid was one which is not included in C-552. Considering that C-552 occurs in cellular periplasmic fraction, this N-terminal sequence is believed to function as a signal peptide for transferring C-552 into the periplasmic fraction (FIG. 2C). It is characteristic that the translation region is rich in GC.

The 5' non-coding region contained sequences corresponding to the -35 region, -10 region and SD region known as a promoter of a procaryote. That is, this portion is the promoter of C-552 (FIG. 2B). Further, the 3' non-coding region contained a palindrome sequence CAGCGGATTA-CATCTG which is considered to be the terminator contributing to termination of the transcription of C-552 (FIG. 2E).

EXAMPLE 2

C-552 gene obtained in Example 1 was expressed in yeast. Japanese Patent Laid-Open No. 37291/1989 details the expression of a heterologous cytochrome C in yeast. Expression of C-552 was conducted by the similar method. Site-specific mutagenesis was conducted by a mutagenesis kit commercially available (BIO-RAD). The synthetic nucleotide employed was prepared on a DNA synthesizer 390A (applied Biosystems).

A DNA fragment of 1.1 kb separated from plasmid pUHTC135 with HindIII and XbaI digestion was ligated into plasmid M13m19 digested with HindIII and XbaI and used to transform *Escherichia coli* MV1190. A single stranded DNA was prepared from the resulting transformant which formed a white plaque. A synthetic nucleotide A249 (5'CGCCCCGTCGACTTACTTTAT3') was annealed to said single stranded DNA and site-specific mutation was induced by using a mutagenesis kit available from BIO-RAD CO., whereby a SalI restriction site was formed in the 3'-side of the termination codon of C-552 gene.

Next, mutation was induced by using synthetic nucleotides A237 (5'TGTTCATTCATGAATTCGGCAAAG3') or A238 (5'TCTTCATGAATTCTACCTC3') as a primer and using the single stranded DNA of the recombinant M13 phage as a template. The mutation by A237 aimed at providing an EcoRI site immediately after the signal peptide of C-552 with simultaneous insertion of ATG, i.e., an initiation codon. The recombinant double stranded M13 DNA carrying the mutation was referred to as M13-12. The mutation by A238 aimed at providing an EcoRI site immediately before the initiation codon ATG of C-552. The recombinant double stranded M13 DNA carrying the mutation was referred to as M13-11. The sequence of the inserted portion of each DNA was determined in a conventional manner to confirm that the expected mutation occurred. Further, it was confirmed that the sequence of C-552 gene had not been changed.

pYHCC101 (Japanese Patent Laid-Open No. 37291/1989) is a shuttle vector between yeast and *Escherichia coli* as well as an expression vector of yeast. This plasmid was originally deposited under the domestic condition with the deposition number FERM p-9475 which was then converted to a deposition under the Budapest Treaty with the deposition number FERM BP-2767 on Feb. 23, 1990. In this plasmid, a human cytochrome C gene is transcribed by yeast glyceraldehyde 3-phosphate dehydrogenase (GPD) promoter. The following procedure was conducted in order to introduce C-552 gene instead of the human cytochrome C gene so as to enable transcription and expression of C-552 gene in yeast. DNA fragments containing C-552 gene, which had been obtained by digesting M13-11 and M13-12 with EcoRI and SalI respectively, were each ligated with a DNA fragment of approximately 8 kb obtained by digesting pYHCC101 with EcoRI and SalI, and transformed into *Escherichia coli* HB101. The plasmids thus obtained were referred to as pYHTC11 and pYHTC12, respectively. Although both of these plasmids contained C-552 gene, the former contained a signal sequence, different from the latter. FIG. 3 outlines the process for the preparation of these plasmids.

Figure 4:
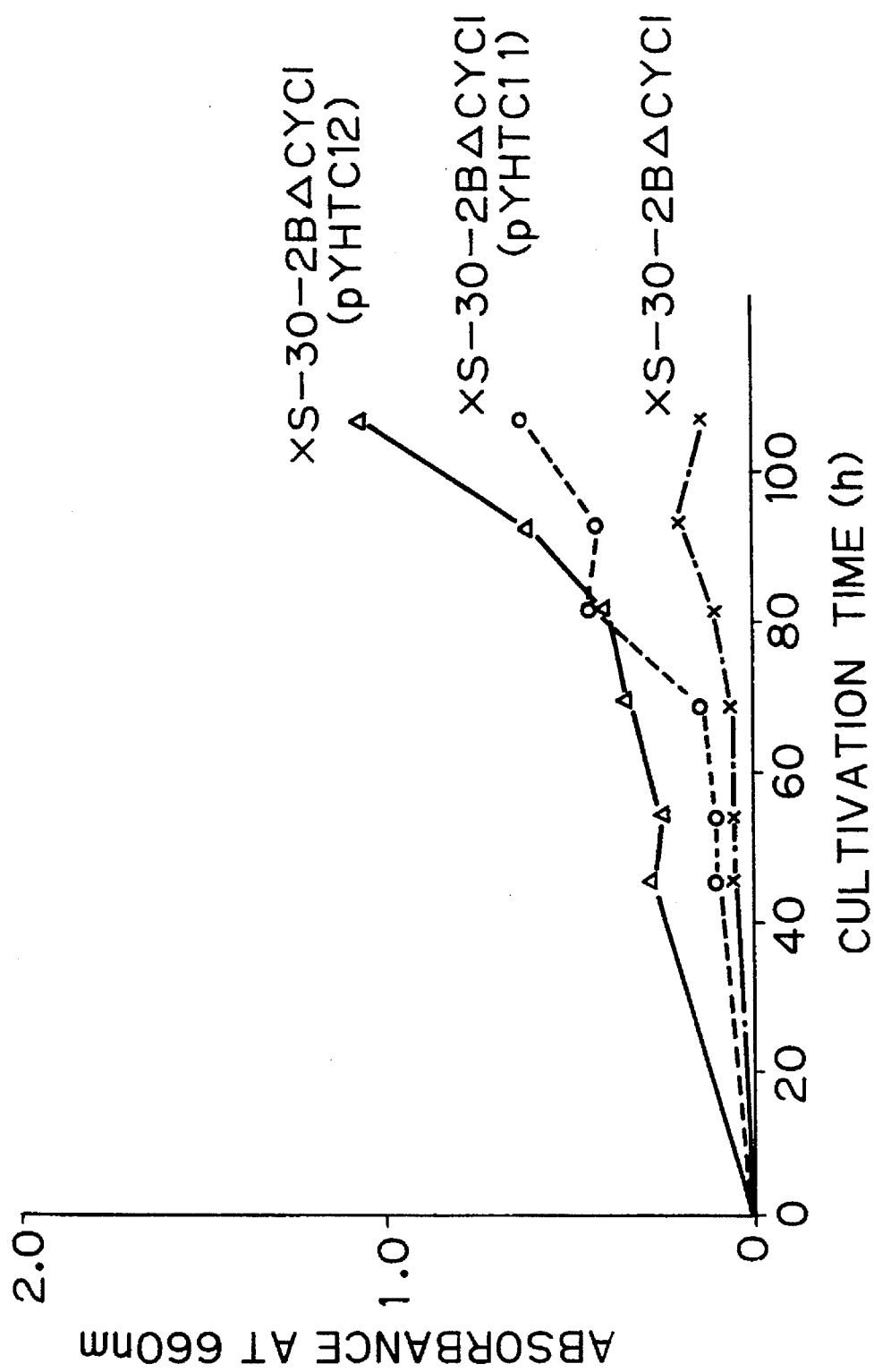
FIG. 4 is a graph showing the growth of yeasts which express C-552 gene using lactic acid as a carbon source.

Yeast strain XS-30-2BΔCYC1 (Matα, trp1, his3, ura3, leu2, cyc1::LEU2) was transformed with the above two plasmids. Then the growth of a transformant having the ability to synthesize tryptophan been recovered was compared with XS-30-2BΔCYC1 in a YNEL medium (0.67% Difco yeast nitrogen base, 0.054 Difco yeast extract, 24 sodium lactate) containing necessary nutrients (histidine, uracil and tryptophan, if required). Namely, each strain was pre-cultured in a YNED medium wherein the sodium lactate in the YNEL medium was replaced with 2% of glucose, and inoculated into the YNEL medium at a density of 1% and the growth was monitored by the absorbance at 660 nm. The results are shown in FIG. 4. Since XS-30-2BΔCYC1 lacked CYC1 coding for iso-1 cytochrome C which is a protein participating in the electron transfer system, it could not utilize lactic acid (a nonfermentative carbon source) and hence could not grow in the YNEL medium. However, the strains transformed with PYHTC11 or PYHTC12 utilized lactic acid and grew, as shown in FIG. 4. These facts may indicate that C-552 (a heterologous protein) was expressed in yeast, and functioned as a component of the electron transfer system. Accordingly C-552 can be obtained from yeast cells by culturing this recombinant yeast.

Next, transformants XS-30-2BΔCYC1 (pYHTC11) and XS-30-2BΔCYC1 (pYHTC12) were cultured. They were cultured in 400 ml of a Burkholder medium (Burkholer, Am. J. Bot., 30, 206, 1943) containing 24 of glucose and 1.5% of sodium lactate as carbon sources under extensive stirring at 30° C. For comparison, XS-30-2B and XS-30-2BΔCYC1 were also cultured under the same conditions. After collecting the cells, each transformant was suspended in 2 ml of water and 1 ml of ethyl acetate by a method reported by Sherman et al. (Sherman et al., J. Biol. Chem., 243, 5446, 1968) and shaken at room temperature over night. The suspension was then centrifuged and the aqueous phase was collected. The cytochrome content and protein content of this fraction were determined. The cytochrome C was determined by measuring the reduced state absorption spectrum by a spectrophotometer (Hitachi 220A) and on the basis of the molecular extinction coefficient at 550 nm (27/mM). On the other hand, the protein level was determined by a BCA protein determination kit (PIERCE). The cytochrome C content in the sample of XS-30-2BΔCYC1 was 0.075 nmole/mg protein, while the strain transformed by pYHTC11 gave the content of 0.48 nmole/mg protein and the strain transformed with pYHTC12 gave the content of 0.40 nmole/mg protein. Since each of the transformants obtained from pYHTC11 and pYHTC12 showed a higher cytochrome C content, C-552 may have been expressed therein.

Then an ethyl acetate extract of each of the above samples was subjected to SDS polyacrylamide gel electrophoresis and subsequent Western Blotting. Next, the expression of C-552 was examined by reaction with an antibody to hydrogen bacterium C-552. The conventional procedure was thereafter followed. For example, refer to Imahori et al. ("Zoku Seikagaku Jikken Koza: Tanpakushitsu no Kagaku", Tokyo Kagaku Dojin, 1987). As a result, the extract of the transformant from pYHTC12 gave a band reacting with the anti-C-552. The molecular weight of this band agreed with that of wild type C-552.

EXAMPLE 3

Expression of Cytochrome C Gene in *Escherichia coli*

Figure 5:
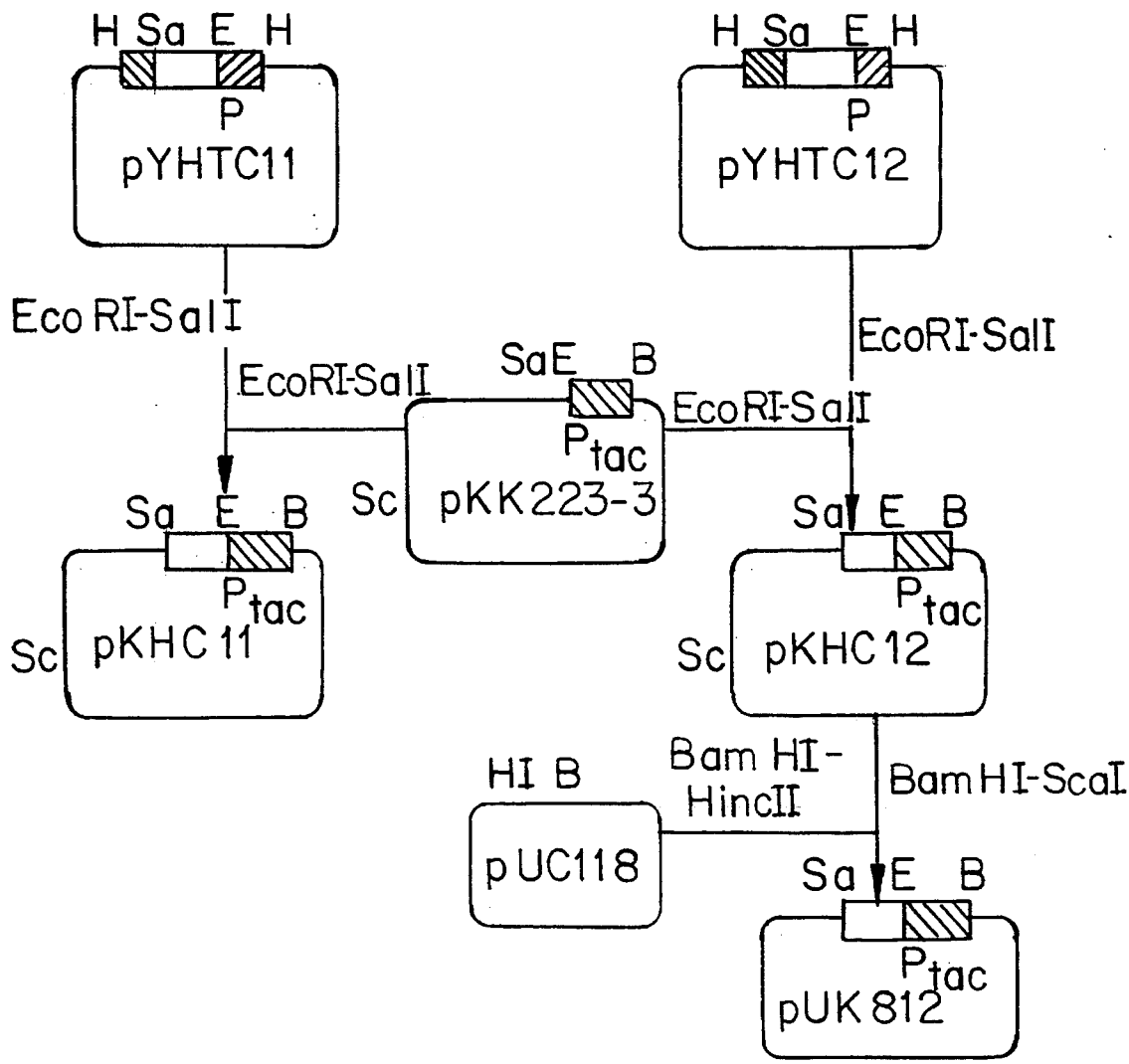
FIG. 5 briefly illustrates the preparation of plasmids employed in the expression of C-552 in *Escherichia coli*.

A DNA fragment containing C-552 gene obtained by digesting pYHTC11 or pYHTC12 with EcoRI and SalI were ligated with a commercially available expression vector for *Escherichia coli*, pKK223-3 (Pharmacia), which had been digested with EcoRI and SalI. In the resulting plasmids, C-552 gene was controlled by tac promoter of *Escherichia coli*. FIG. 5 illustrates the construction of these plasmids. The plasmid from pYHTC11 was referred to as pKHC11 while that from pYHTC12 was referred to as pKHC12. Furthermore, a fragment containing C-552 gene was screened from among DNA fragments obtained by digesting pKHC12 with BamHI and ScaI. This fragment was ligated into pUC118 (Takara Shuzo) digested with BamHI and HincII. The plasmid thus formed was referred to as pUK812. In the construction of these plasmids, JM109 was employed as an *Escherichia coli* host.

2 ml cultures each of the transformants JM109 (pKHC11), JM109 (pKKHC12) and JM109 (pUK812) were prepared in an L medium and then a 1 ml aliquot was inoculated into 1.2 l of a medium containing nitrate (1% of glucose, 0.08% of sodium nitrate, 50 mM of monosodium carbonate, 0.01% of magnesium sulfate, 0.7% of monopotassium phosphate, 0.05% of trisodium citrate, 0.1% of ammonium sulfate, 1 μg/ml of thiamine, 12 μM of ammonium molybdate, 1 μM of selenic acid, 12 mM of iron citrate, 0.5% of bactopeptone, pH 7.0) and stationarily cultured at 37° C. for 24 hours. During this culture, isopropyl-β-D-thiogalactopyranoside (IPTG) was added, if required, as an expression inducer at a final concentration of 0.5 mM. After completion of the culture, the cells were collected and subjected to the following procedure.

Figure 6B:
FIGS. 6A and 6B represent photographs showing the results of detection of C-552 expressed in yeast and in *E. coli*, respectively, with the use of an anti-C-552 antibody.
Figure 6A:
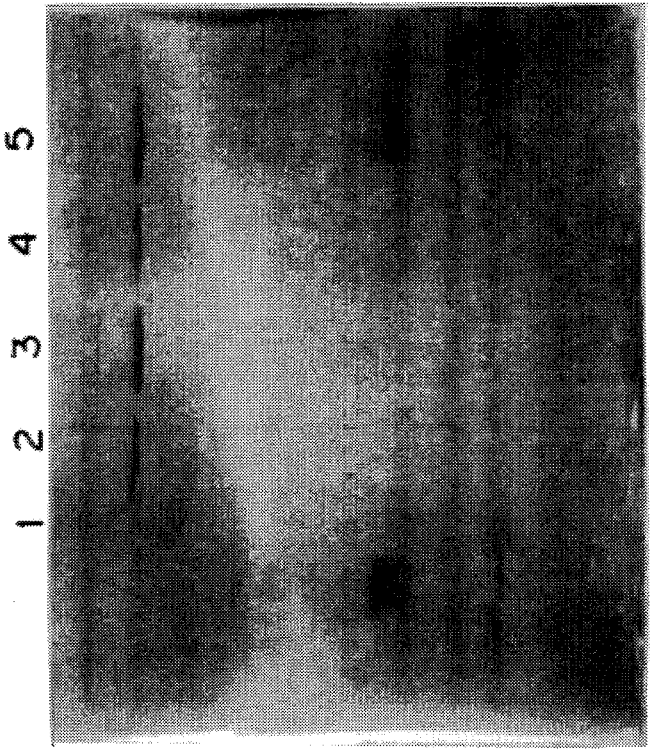

The cells were homogenized and subjected to SDS polyacrylamide gel electrophoresis followed by Western blotting. C-552 on the blot was detected with the use of anti-C-552 antibody. FIG. 6 shows the results. JM109 (pKHC12, +IPTG), among the examined transformants JM109, JM109 (pKHC11, −IPTG), JM109 (pKHC11, +IPTG), JM109 (pKHC12, −IPTG) and JM109 (pKHC12, +IPTG), exclusively showed the specific band at the same position as that of the wild type C-552. These results indicate that C-552 protein was expressed in *Escherichia coli*. It was unexpectedly noted that transformants from pKHC11 containing the gene including the coding region for the signal peptide of C-552 did not react with the above-mentioned antibody while the transformant from pKHC12 containing a gene free from any signal peptide exclusively showed the expression. Furthermore, the cells of JM109 (pKHC12, +IPTG) were fractionated and the localization of C-552 in the cells was examined. C-552 was found in cytoplasma.

In order to examine expression level of C-552, the cells cultured in the above-mentioned manner were disrupted in a French press and the protein and cytochrome C levels in the soluble fraction were determined. The content of C-552 in JM109 (pKHC12, +IPTG) and JM109 (PUK812, +IPTG) amounted to approximately 0.4% of the total proteins.

The recombinant C-552 was then isolated from JM109 (pUK812, +IPTG) cells by a known method (Y. Sanbongi et al., J. Bacteriol., 171, 65, 1989). To be more specific, the cells were harvested and washed with 50 mM phosphate buffer, pH 7.0. The cell suspension was thawed and the cells were disrupted by one passage through French pressure cells (1000 kg/cm$^2$). Cell-free extract was obtained by ultracentrifugation (100,000×g, 1 hr) of the disrupted cells. After removal of nucleic acids, said extract was condensed by means of ultrafiltration using an ultra filter having a molecular weight cut-off of 1000. The condensed solution was dialyzed against 10 mM phosphate buffer (pH 7.0). The dialyzed solution was put on a column of CM-Toyopearl 650S (Toso Corp., Tokyo) pre-equilibrated with 10 mM phosphate buffer (pH 7.0). The column was washed with the same buffer and then eluted with a linear gradient of NaCl (0–300 mM) in the same buffer. The eluate was then fractionated. A small amount of each fraction was reduced with dithionite, and its absorption at 552 nm was measured spectrophotometrically. Fractions showing absorbance above 0.1 O.D. unit were collected and dialyzed against 10 mM phosphate buffer (pH 7.0). The dialyzed solution was on a column of Dye matrex Green A (Amicon Far East, Ltd.) pre-equilibrated with 10 mM phosphate buffer (pH 7.0). The column was washed with the same buffer and then eluted with a linear gradient of NaCl (0–300 mM) in the same buffer, and the absorbance at 552 nm was monitored to collect C-552 fractions.

EXAMPLE 4

Properties of Recombinant Cytochrome C-552

The absorption spectrum, heat stability and enzymological properties of the purified C-552 agreed with those of wild type C-552. Now the properties of the purified C-552 will be described.

Properties of Recombinant Cytochrome C-552

Figure 7A:
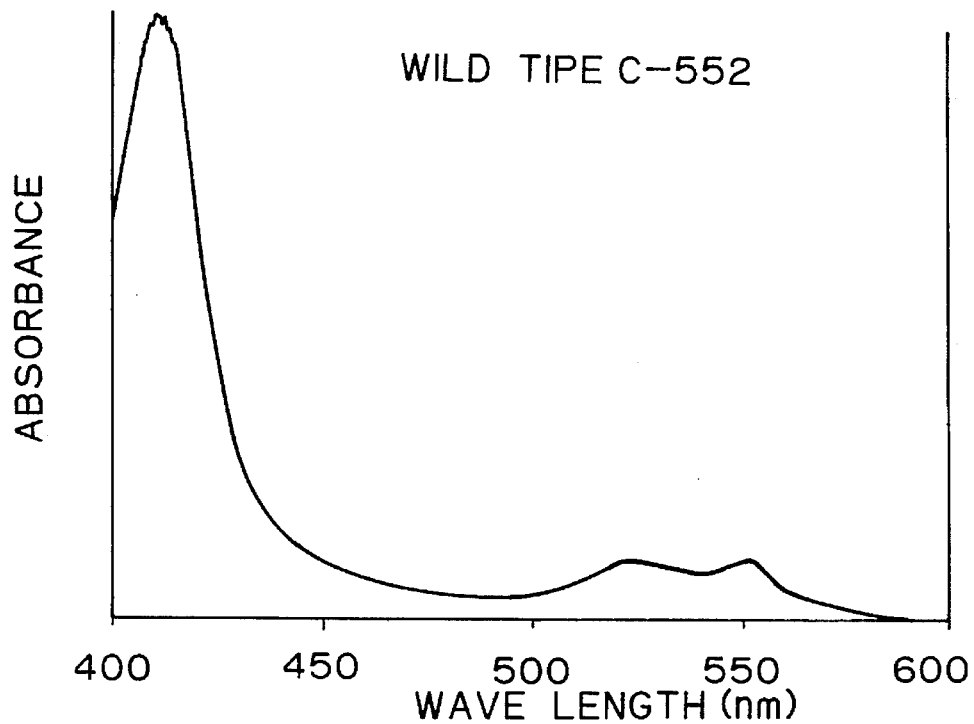
FIGS. 7A and 7B show the absorption spectra of wild type cytochrome C-552 and recombinant cytochrome C-552, respectively in reduced form.
Figure 7B:
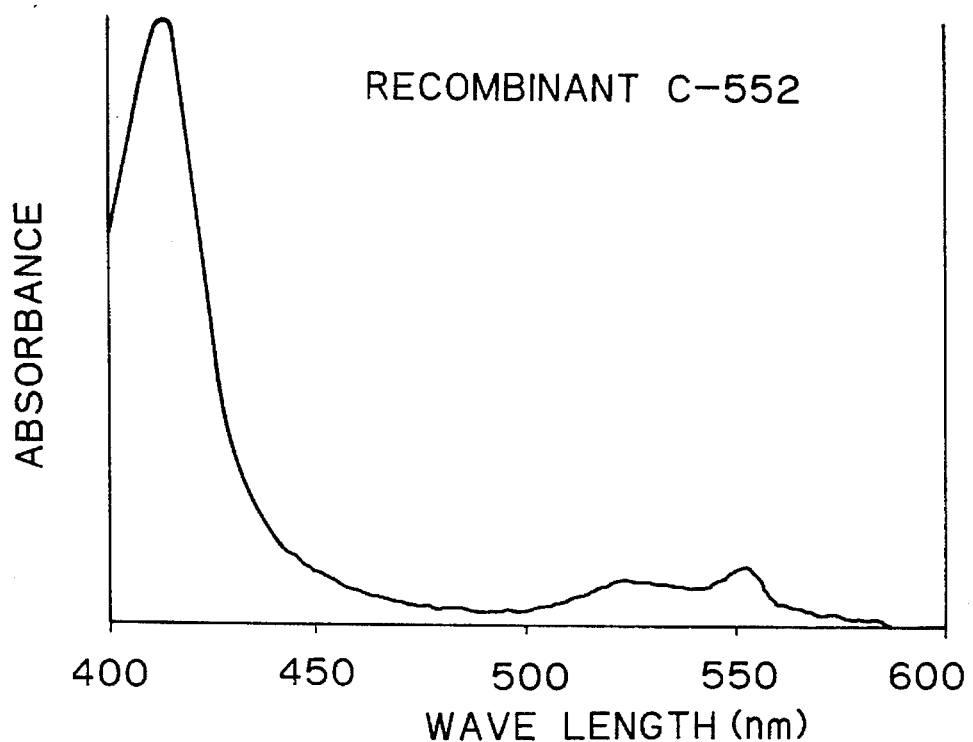

FIG. 7 shows the comparison of the absorption spectrum of the recombinant cytochrome C-552 in reduced state thus purified with that of wild type cytochrome C-552. As FIG. 7 shows, the two absorption spectra agreed with each other. It is well known that the absorption spectrum of cytochrome C reflects the higher structure of the molecule. Therefore the recombinant cytochrome C-552 had the same structure as that of the wild type cytochrome C-552, though the former carried a methionine residue in the amino terminal.

Furthermore, the circular dichroism (CD) of the recombinant cytochrome C-552 was determined in order to examine the structure thereof. The determination of CD enables estimation of the secondary structure of a protein molecule. Cytochrome C-552 was dissolved in 10 mM KH$_2$PO$_4$—NaOH (pH 7.0) in such a manner as to give a concentration of 50 μg/ml. Then the CD spectrum at 210 to 250 nm was determined by JASCO automatic recording spectro-polarimeter Model J-20 (Nippon Bunko, Japan). Separately, a portion of the cytochrome C solution was treated in an autoclave at 120° C. for 10 minutes and then cooled to room temperature. The CD spectrum of this solution was also determined. FIG. 8 shows the results, wherein A is CD spectrum determined before autoclaving while B is that determined after the heating. FIG. 8 indicates that the recombinant C-552 has the same structure as that of the wild type C-552 and further that neither the recombinant C-552 nor the wild type C-552 is subjected to any change in their structures by autoclaving. That is to say, the C-552 obtained by the recombinant technique is highly stable under heating, which is advantageous from an industrial viewpoint. In contrast to this, equine cytochrome C showed a remarkable change in the CD spectrum after the autoclaving, suggesting that it was completely denatured.

EXAMPLE 5

Analysis on the Amino Acid Sequence of Recombinant Cytochrome C

The amino acid sequence in the amino terminal of the recombinant C-552 was analyzed by a gas phase sequencer (Applied Biosystems). As a result, it was determined to have the following sequence:

Met-Asn-Glu-Gln-Leu-Ala-Lys-Gln-Lys-Gly-.

This sequence agreed with the amino terminal sequence of wild type C-552, except that a methionine residue was added to the amino terminal. The presence of the methionine residue did not damage the preferable properties of C-552. Therefore it is believed that the process described herein enables the economical production of a large amount of recombinant C-552. The promoter and *Escherichia coli* host used herein are cited merely by way of examples and the expression can be conducted by using other promoters and hosts.

*Hydrogenobacter thermophilus* C-552 gene was cloned and the nucleotide sequence thereof was determined. Furthermore, this gene was linked to expression vectors of yeast and introduced into yeast hosts which could not utilize lactic acid. As a result, the capability of utilizing lactic acid was restored and the content of cytochrome C was elevated. Namely, C-552 was expressed in the yeast. C-552 was also expressed in *E. coli* by using and *E. coli* expression vector. The recombinant C-552 produced by these recombinant microorganisms had the excellent properties which are the same as those of the authentic C-552. In a similar fashion, it will be possible to produce recombinant C-552 by many other host microorganisms. Thus a large amount of C-552 can be obtained without difficulty through DNA recombinant techniques. In addition, yeast can express not only cytochromes C of a eucaryote but also those of a procaryote differing in structure.

Furthermore, the structures of the promoter, terminator and signal peptide, which are characterized by their ability function at a high temperature, have been clarified.

What is claimed is:

1. Yeast or *E. coli* cells transformed with a plasmid which contains a DNA sequence encoding thermophilic cytochrome C-552, wherein the nucleotide sequence of said DNA is:

AATGAACAGCTTGCCAAGCAAAAGGGCTGTATGGCTT
GCCACGATCTGAAAGCTAAGAAGGTGGGACCTGCTTA
CGCAGATGTAGCTAAGAAGTATGCGGGAAGAAAGGA
TGCTGTTGATTATCTGGCTGGCAAGATAAAGAAGGGC
GGTTCTGGTGTGTGGGGTTCTGTTCCCATGCCTCCTCA
AAATGTAACCGATGCGGAAGCAAAACAGCTTGCCCAG
TGGATACTCTCCATAAAG[TAAG].

2. A process for the production of C-552 which comprises culturing the yeast or *E. coli* cells of claim 1 and purifying C-552 secreted by said cells.

3. The process of claim 2 wherein the yeast or *E. coli* cells are cultured under aerobic conditions.

* * * * *